United States Patent [19]

Cecil, Jr. et al.

[11] Patent Number: 4,766,887
[45] Date of Patent: Aug. 30, 1988

[54] DISPOSABLE VAGINAL SPECULUM

[75] Inventors: John Cecil, Jr., Skaneateles; Robert R. Black, Syracuse, both of N.Y.

[73] Assignee: Welch Allyn, Inc., Skaneateles Falls, N.Y.

[21] Appl. No.: 876,211

[22] Filed: Jun. 19, 1986

[51] Int. Cl.$^4$ .............................................. A61B 1/32
[52] U.S. Cl. ..................................... 128/17; 128/345
[58] Field of Search ...................... 128/17, 18, 19, 20, 128/303.11, 345, 341, 342, 343; 403/67, 116; D24/18

[56] References Cited

U.S. PATENT DOCUMENTS

| | | | |
|---|---|---|---|
| 1,300,756 | 4/1919 | Moyer | 128/17 |
| 3,246,646 | 4/1966 | Murphy | 128/17 |
| 3,332,414 | 7/1967 | Gasper | 128/17 |
| 3,528,409 | 9/1970 | Bruder | 128/17 |
| 3,568,665 | 3/1971 | Lindgren et al. | 128/17 |
| 3,650,266 | 3/1972 | Pestka et al. | 128/17 |
| 3,716,047 | 2/1973 | Moore et al. | 128/18 |
| 3,752,149 | 8/1973 | Ungar et al. | 128/20 |
| 3,890,961 | 6/1975 | Moore et al. | 128/17 |
| 3,985,125 | 10/1976 | Rose | 128/17 |

Primary Examiner—Richard C. Pinkham
Assistant Examiner—Mark S. Graham
Attorney, Agent, or Firm—Wall and Roehrig

[57] ABSTRACT

A two-piece vaginal speculum has upper and lower blade members pivotally connected to each other by a slot and pin arrangement for relative pivotal and spatial adjustment of the blade members. Slots are formed in the sides of the upper blade member, and trunnions with lugs directed outwardly through the slots are formed on the sides of the lower blade member. Cheek plates in the upper blade member sides have ribs formed therein for selective engagement with teeth formed on cheek plates of the lower blade member sides. The ribs extend in the direction generally parallel to the slots, and achieve sliding engagement with the teeth so that the position of the trunnion lugs can be moved from one to another set of notches formed on the slots. The teeth and rib have engaging surfaces which are back angled at about seven degrees so that compressive forces of the patient's vaginal wall on the blades will urge the rib and the engaging tooth, and their supporting cheek plates, into engagement. The lug and the slot notches are similarly back angled. A yoke formed on the upper blade member permits elevational adjustment up or down under a practitioner's thumb pressure.

10 Claims, 2 Drawing Sheets

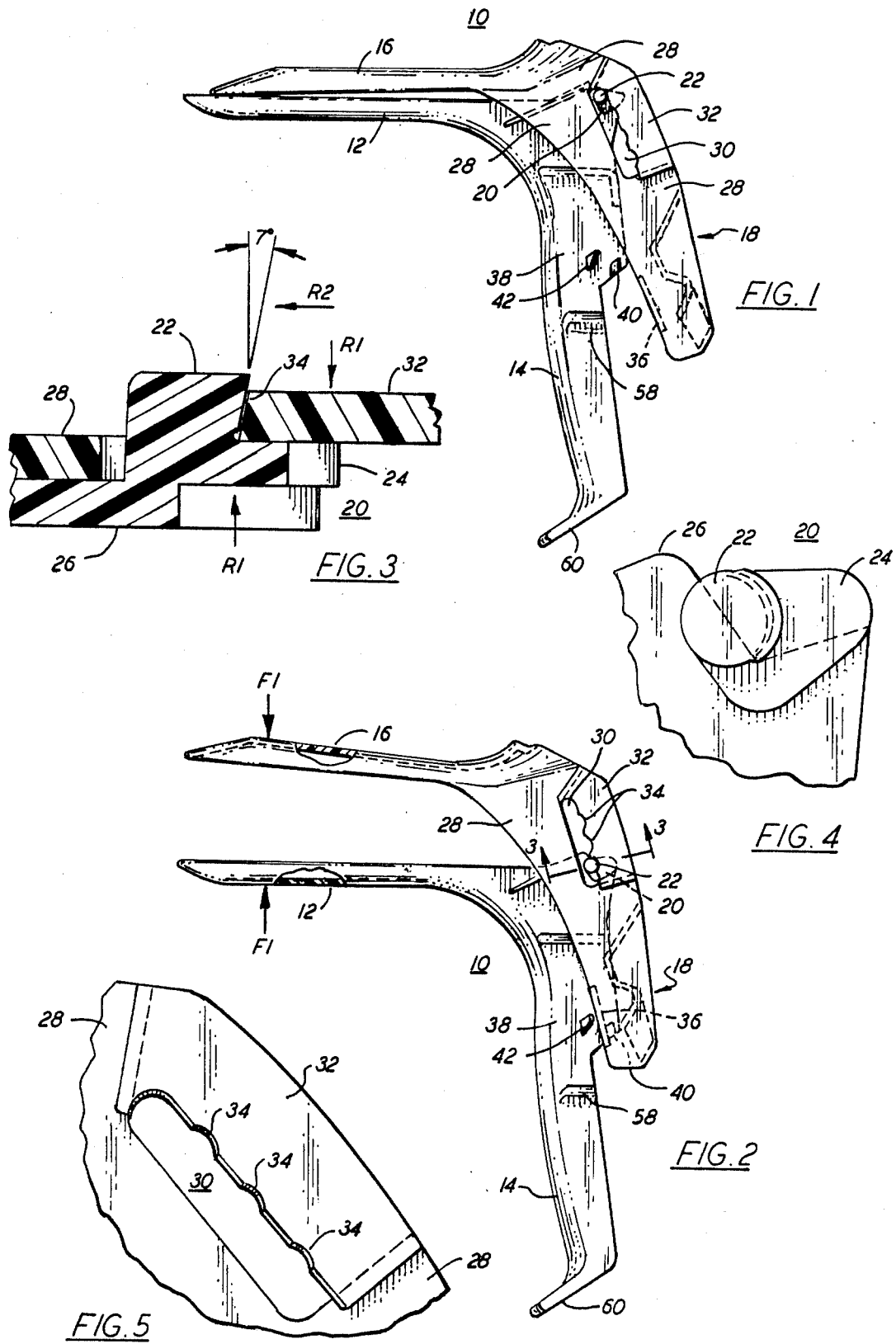

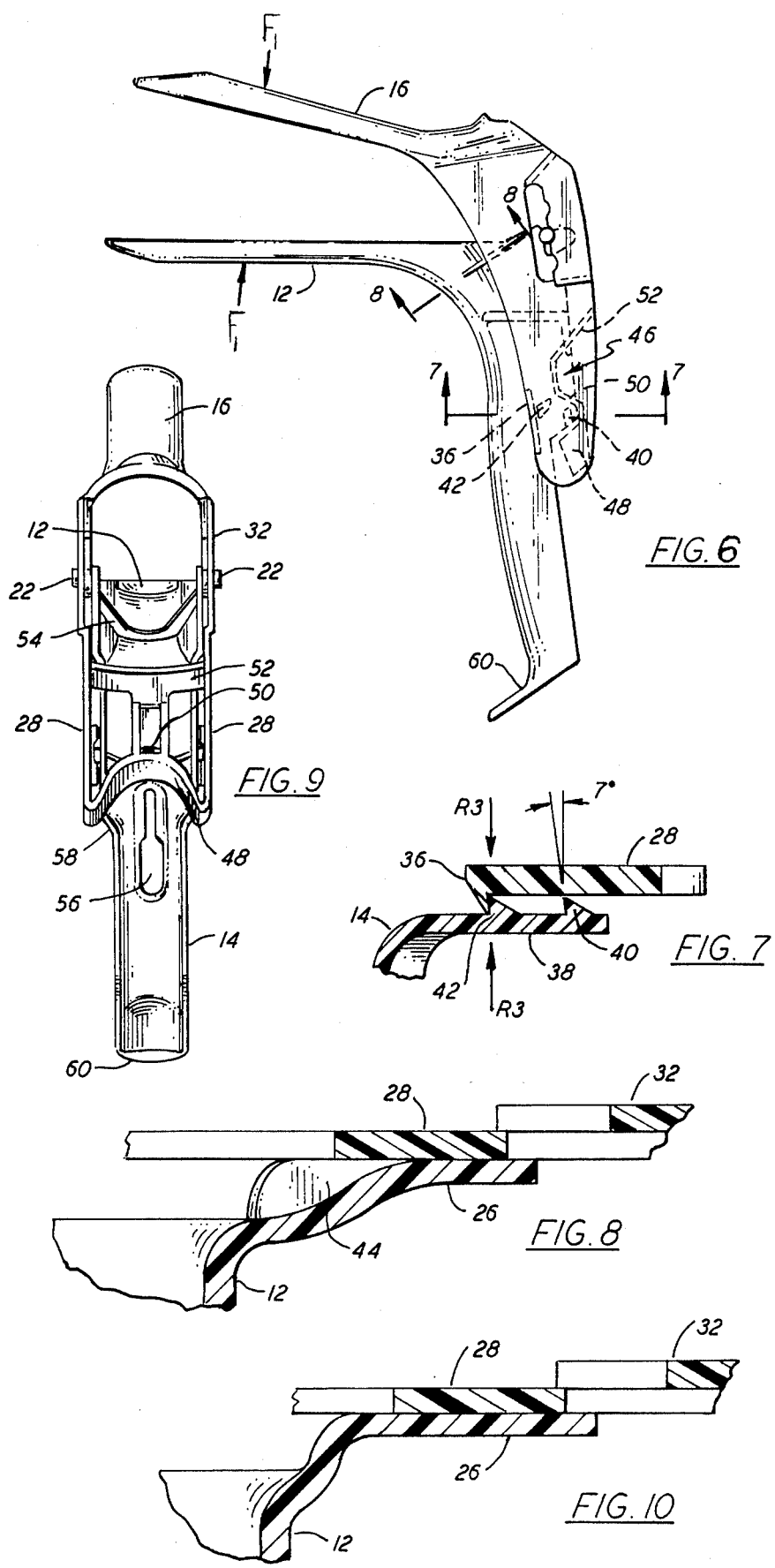

DISPOSABLE VAGINAL SPECULUM

BACKGROUND OF THE INVENTION

This invention relates generally to medical or surgical instruments, and is more particularly directed to a two-piece disposable vaginal speculum.

Many disposable, plastic vaginal specula of this general type have been previously proposed, typically employing a Graves or Peterson blade. These are often formed of a moldable synthetic resin such as polystyrene or polypropylene and can be clear or colored. These disposable vaginal specula are particularly useful for high-volume clinical users, such as clinics which specialize in the detection of venereal disease or cancer of the cervix. Because the practitioner or clinician should have both hands free during an examination, the vaginal speculum is preferably lockable at any of several open positions, and then easily released for removal. The speculum should have at least five open positions. Generally, certain lubricants for the speculum are not favored, because they can spoil a pap smear application, so a plastic material is generally employed for which water or silicone solution provides a satisfactory lubricant.

It is desirable that the design of the speculum be simple to reduce molding and tooling costs. In particular, these specula should be constructed with a minimum number of parts, ideally, only an upper and lower part.

However, there has been a problem in constructing such a speculum which will reliably remain in an open, locked position. This arises when the pressure exerted on the blade by the vaginal wall distorts the locking parts of the speculum, which, in order to be low-cost and disposable, is constructed of plastics material that is distorted by pressure.

Another problem of prior-art vaginal specula is that they often produce noisy clicks when being opened within the patient. This noise is caused by the ratchet action of the speculum. Although the ratchet action itself is not harmful, the clicking noise is always disturbing to the patient, and sometimes causes a traumatic reaction, making examination more difficult.

Typical vaginal specula are disclosed, for example, in U.S. Pat. Nos. 3,568,665 of Mar. 9, 1971 and 3,752,149 of Apr. 18, 1973. A three-part disposable speculum is shown in U.S. Pat. No. 3,716,047 of Feb. 13, 1973, and several two-part disposable specula are shown in U.S. Pat. Nos. 3,246,646 of Apr. 19, 1966; 3,332,414 of July 25, 1967; 3,650,266 of Mar. 21, 1972; 3,985,125 of Oct. 12, 1976; and 3,890,961 of June 24, 1975.

OBJECTS AND SUMMARY OF THE INVENTION

Accordingly, it is an object of this invention to provide a disposable vaginal speculum which is both inexpensive and simple to operate.

It is another object of this invention to provide such a speculum which reliably locks in an open position to permit examination.

It is another object of this invention to provide a disposable vaginal speculum which can be moved from an insertion position to one or more open positions without a great deal of disturbing clicking sounds.

It is yet another object of this invention to provide a disposable vaginal speculum in which the compressive force of the vaginal wall on the blades of the speculum urges the mating parts of the two blades into a more secure locking contact with each other.

It is still another object of this invention to provide a disposable vaginal speculum with great lateral stability, and having a maximum inside width at its proximal end while also having a minimum outside width.

In accordance with one aspect of this invention, a two-piece vaginal speculum is comprised of an upper blade member and a lower blade member that is pivotally connected to it by a slot and pin arrangement. This arrangement permits both pivotal and spatial adjustment of the blade members. The slots are formed in the sides of one of the blade members, for example, the upper blade member. Corresponding trunnions are formed on the facing sides of the other blade member, that is, the lower blade member, with the trunnions each having a lug penetrating an associated one of the slots in the upper blade walls. The slots each have a number of notches along one side in which the lugs may be reposed to define pivot axes for the blade members at a number of spaced positions. One of the blade members has a longitudinal slide member that extends generally in the same direction as the slots, and the other of the blade members has a number of teeth that selectively engage the slide member. The slide member and the selected tooth combine to define a selected degree of opening of the speculum blade members. The engaged tooth is slidable with respect to the slide member so that the upper blade can be elevated with respect to the lower blade member thereby permitting movement of the trunnion lugs from one of the sets of slot notches to another. Cheek plates of the upper and lower blade members press against the teeth and slide member, respectively, for increased lateral stability.

The engaging surfaces of the teeth and the slide member are back angled, for example, by about seven degrees, so that the compressive force on the blade will tend to urge the facing walls of the two blade members towards one another. Similarly, the notches in the slots and the engaging arcuate surfaces of the trunnion lugs are also back angled at about seven degrees so that the compressive force on the speculum blades will tend to urge the lugs in the direction into the slots.

A yoke at the proximal end of the upper blade member has a curved thumb plate for elevating, or spatially opening the speculum by a practitioner's thumb pressure, a pull-down plate connected to the thumb plate and extending distally and upwards therefrom for spatially closing the blades, and a tee portion connected to the pull-down plate and extending upwards and proximally from the pull-down plate, with the lateral arms of the tee portion being connected to opposite sides of the upper blade member.

The above and many other objects, features, and advantages of this invention will be more fully understood from the ensuing detailed description of a preferred embodiment, which should be considered in connection with the accompanying drawing.

BRIEF DESCRIPTION OF THE DRAWINGS

FIG. 1 is a side elevation of a vaginal speculum according to a preferred embodiment of this invention, the speculum being shown in a closed or insertion position.

FIG. 2 is a side elevation of the preferred embodiment, here shown in an open elevated position and disposed at a first angular position.

FIG. 3 is a cross section taken at the line 3—3 of FIG. 2.

FIG. 4 is a detail of the trunnion of the preferred embodiment.

FIG. 5 is a detail of the slot and side wall arrangement of the preferred embodiment.

FIG. 6 is a side elevation of the preferred embodiment shown partly open and in a second angular position.

FIG. 7 is a cross section taken at the line 7—7 of FIG. 6.

FIG. 8 is a cross section taken at line 8—8 of FIG. 6.

FIG. 9 is a rear elevation of the preferred embodiment when in the position shown in FIG. 6.

FIG. 10 is a partial cross section of an alternative arrangement.

DETAILED DESCRIPTION OF THE PREFERRED EMBODIMENT

With reference to the drawing figures, and initially to FIGS. 1-4 thereof, a two-piece disposable vaginal speculum 10 is shown to have a lower blade 12 with a handle 14 at the proximal end thereof and extending downwards, and an upper blade 16 with a proximal portion 18 for achieving elevational and angular adjustment. The blades 12 and 16 here are of the Graves type and, according to the usual convention, the lower blade 12 protrudes slightly beyond the distal end of the upper blade 16.

This vaginal speculum 10 has a slot-and-pin arrangement for achieving angular and elevational or spatial opening of the blades 12 and 16.

On each side of the lower blade 12 there is a trunnion 20, having an outwardly projecting lug or pin 22 supported on a trunnion plate 24, the plate 24 being fused to a side wall 26 of the lower blade 12.

The upper blade 16 has side walls or cheek plates 28 opposed to the side walls 26 of the lower blade 12, and, as shown in FIG. 5, a generally longitudinal slot 30 is formed in each of the side walls or cheek plates 28, with a side plate 32 being offset from the associated cheek plates 28 (See FIG. 3) and forming the proximal edge of the slot 30. A plurality of notches 34 are disposed along the proximal wall of the slot 30 in the plate 32. In this embodiment there are three such notches 34 at spaced positions between the ends of the slot 30. However, a larger or smaller number could be employed.

The cheek plates 28 of the proximal portion 16 of the upper blade 16 each have a rib 36 extending in a direction generally parallel to the slot 30. These ribs 36 serve as slides. As shown in cross section in FIG. 7, the rib has a sloping distal surface and an engaging proximal surface which has a slight back angle, here, about seven degrees.

The handle portion 14 of the lower blade 12 has parallel side or cheek plates 38, on outer surfaces of which there are disposed a first tooth 40 and a second tooth 42. The more distal tooth 42 is offset upwards from the more proximal tooth 40. These teeth 40 and 42 engage with the rib or slide 36 to define a first angular position (FIG. 2) of the speculum 10 and to define a second angular position (FIG. 6), respectively. As shown again in FIG. 7, the first tooth 40 and the second tooth 42 are inclined on the proximal surfaces thereof and have a slight back angle (i.e. seven degrees) on their distal surfaces which engage the rib 36. The cheek plates 28 and 38 laterally engage the ridges of the rib 36 and teeth 40, 42. This produces great lateral stability while permitting the cheek plates 28 and 38 to be made as thin as possible.

Returning to FIG. 3, it will be seen that the notches 34 of the slot 30 and the engaging surface of the trunnion lug 22 are similarly inclined at a back angle of about seven degrees.

The slight back angle of the engaging surfaces of the teeth 40, 42 and the slide rib 36, and of the notches 34 and the lug 22 serve to draw the meeting parts of the speculum blades 12 and 16 towards one another under the compressive forces on the blades during examination. The compressive force $F_1$ (FIGS. 2 and 6) on the blades 12 and 16 produce resultant forces R which tend to urge the trunnion plate 24 against the side plate 32 (FIG. 3) in reaction to a transmitted force vector $R_2$ between the back-angled notch 34 and the back-angled facing extended arc of the trunnion lug 22. This produces greater mechanical stability and resistance to twisting under compression on the blades 12 and 16. Similar resultant forces $R_3$ (FIG. 7) urge the cheek plates 28 and 38 into contact with the teeth 40, 42 and the rib 36. Because of this feature, the self-locking elements produce an increased structural strength with a minimum lateral cross-section of the structural members. A smaller overall width of the speculum 10 is achieved. This back-angling of the elements 22, 34, 36, 40, and 42 also prevents the undesired snapping closed of the speculum 10 during examination, which sometimes occurs when prior-art types of disposable specula are used.

As shown in FIG. 8, a reinforcing rib 44 is provided on each wall 26 of the lower blade 12, generally radiating from the position of the trunnion lug 22. This rib 44 serves to support the side wall or cheek plate 28 of the upper blade 16, as the cheek plate slides past the reinforcing rib.

As shown in the rear view of FIG. 9, the proximal portion 18 of the upper blade 16 has a yoke 46 which not only provides additional support between the cheek plates 28 of the upper blade 16, but also serves for achieving elevational and angular positional changes under thumb pressure. This yoke 46 has a generally U-shaped thumb plate 48 rising from the lower edges of the cheek plates 28, and a pull-down plate portion 50, extending distally upwards from the proximal upper edge of the thumb plate. A tee portion 52 is connected to the pull-down plate 50 and has lateral arms fused to inner surfaces of the plates 28.

The handle portion 14 of the lower blade 12 includes a rib 54 which can serve as a mucus trap, a keyway 56 for attaching an optional lighting instrument, a reducer 58 where the width dimension of the handle 14 changes, and a toepiece 60 at the lower end of the handle 14.

The inclined proximal surfaces of the teeth 40 and 42 and the inclined distal surfaces of the slide rib 36 permit the rib 36 and the teeth 40, 42 to snap over one another. Accordingly, at any given elevational position as defined by the lugs 22 and notches 34, the speculum 10 can be moved from one angular position to the next wider one, i.e., from that of FIG. 1 to that of FIG. 2, or from that of FIG. 2 to that of FIG. 6.

It has been found that the vaginal speculum of this embodiment is rather quiet, and is moved from one spatial position to another without a disagreeable amount of clicking noise. The back angle of seven degrees in the lug 22 and notches 34 and in the rib 36 and the teeth 40, 42 ensures that under the force $F_1$ of the vaginal wall against the blades 12 and 16 the locking parts of this speculum 10 are urged into secure engagement with one another. Still further, the design of this speculum 10 facilitates its molding at lesser expense than in the molds employed with prior art specula. Thus the specula 10 of this invention can be manufactured at low enough cost that they can be considered disposable, single-use items.

As an alternative to the structure shown in FIG. 8, the rib 44 can be omitted, and the side wall 26 reconfigured as shown in the alternative arrangement of FIG. 10.

Although the invention has been described in detail with reference to one embodiment, it should be recognized that the invention is certainly not limited to that embodiment, and that many modifications and variations can be effected therein without departure from the scope and spirit of the invention, as defined in the appended claims.

We claim:

1. Two-piece vaginal speculum comprising
    an upper blade member and lower blade member pivotally connected thereto by a slot and pin arrangement to permit relative pivotal and spatial adjustment of the blade members, with slots being formed in sides of one of the blade members, and corresponding trunnions being formed on facing sides of the other blade member, the trunnions each having a lug penetrating an associated one of the slots; said slots each having a plurality of notches therein wherein said lugs may be reposed defining pivot axes for said blade members, one of said blade members having a longitudinal slide member extending generally in the direction of said slots and the other of said blade members having a plurality of teeth for selectively engaging said slide member to define respective degrees of opening of said speculum blade members, the engaged teeth being slideable along said slide member to permit spatial adjustment of said trunnion lugs from one set of the notches of said slots to another,
    wherein each of the blade members has a pair of spaced side walls extending proximally and downwardly, the pair of side walls of one blade member being disposed to fit between the pair of side walls of the other blade member, and
    wherein said slide member extends along the side walls of one blade member and said teeth are disposed in the facing side wall of the other blade member, the slide member and teeth having mating surfaces angled at an angle from normal with respect to said surfaces, so as to urge the facing side walls of the blade members towards one another.

2. The speculum of claim 1 wherein said angle is substantially seven degrees.

3. The speculum of claim 1 wherein the side walls of the upper blade include offset plates defining said slots at distal sides of said plates, and said trunnions each have a plate whose thickness is substantially the distance of the offset from the side walls to the offset plates.

4. The speculum of claim 1 wherein mating surfaces of said trunnion lugs and said notches of said slots are back angled at a predetermined angle from normal with respect to said side walls so as to urge the lugs into said slots.

5. The speculum of claim 4 wherein said angle is substantially seven degrees.

6. The speculum of claim 1 wherein the more distal of said teeth is offset upwards from the more proximal of said teeth.

7. The speculum of claim 1 wherein said teeth have sloping proximal surfaces and said slide member has a sloping distal surface so that said slide member can be moved from engagement with one of said teeth to engagement with the next of said teeth by springing movement over the teeth to permit the blade members to be opened wider without changing the position of the trunnion lugs in said slots.

8. Two-piece vaginal speculum comprising an upper blade member and a lower blade member pivotally connected thereto by a slot and pin arrangement to permit relative pivotal and spatial adjustment of the blade members, with slots being formed in sides of one of the blade members, and corresponding trunnions being formed on facing sides of the other blade member, the trunnions each having a lug penetrating an associated one of the slots; said slots each having a plurality of notches therein wherein said lugs may be reposed defining pivot axes for said blade members, one of said blade members having a longitudinal slide member extending generally in the direction of said slots and the other of said blade members having a plurality of teeth for selectively engaging said slide member to define respective degrees of opening of said speculum blade members, the engaged teeth being slideable along said slide member to permit spatial adjustment of said trunnion lugs from one set of the notches of said slots to another, and wherein said upper blade member includes a yoke at its proximal end, said yoke having a curved thumb plate connected to downward-most ends of the sides of the upper blade member, a pull-down plate connected to the thumb plate and extending distally and upwards therefrom, and a tee portion connected to said pull-down plate extending upwards and proximally from said pull-down plate, and with lateral arms of said tee portion being connected to the opposite sides of said upper blade member.

9. A two-part disposable vaginal speculum capable of angular and elevational adjustment comprising an upper blade member and a lower blade member pivotally connected thereto by a slot and pin arrangement to permit relative pivotal and spatial adjustment of the blade members, with slots being formed in the sides of one of the blade members and corresponding trunnions being formed on facing sides of the other blade member and each having a lug penetrating an associated one of said slots, the speculum including slide means in one of said blade members and tooth means in the other of said blade members engaging said slide means at any of a plurality of angular settings of said blade members, and permitting sliding movement at such angular settings; and notch means in said slots for establishing a plurality of elevational positions of said blade members relative to one another, said notch means and mating surfaces of said lugs being back angled to engage each other with additional force under compressive force of said blades, and wherein said slide means has a sloping distal surface so that the slide means can be moved from engagement with said tooth means at one said angular setting by springing movement over the tooth means to permit the blade members to be opened to a wider angular setting at a given elevational setting without changing to another elevational setting, and a reversely sloping proximal surface for positively engaging said tooth means at said wider angular setting to prevent return to a narrower angular setting.

10. The speculum of claim 9 in which said notch means define at least three said elevational positions.

* * * * *